United States Patent [19]
Duhaylongsod et al.

[11] Patent Number: 6,113,588
[45] Date of Patent: Sep. 5, 2000

[54] TRANSILLUMINATION CATHETER AND METHOD

[75] Inventors: Francis G. Duhaylongsod, Durham, N.C.; Hugh L. Narciso, Jr., Mountain View, Calif.

[73] Assignees: Corvascular, Inc., Palo Alto, Calif.; Duke University, Durham, N.C.

[21] Appl. No.: 09/042,433

[22] Filed: Mar. 13, 1998

[51] Int. Cl.[7] ................................................. A61B 18/18
[52] U.S. Cl. .................................... 606/15; 606/2; 607/89
[58] Field of Search ......................... 606/2, 8, 13, 14–17; 607/89, 92–93, 88

[56] References Cited

U.S. PATENT DOCUMENTS

| | | |
|---|---|---|
| 5,042,980 | 8/1991 | Baker et al. . |
| 5,169,395 | 12/1992 | Narciso, Jr. . |
| 5,176,881 | 1/1993 | Sepaniak et al. . |
| 5,196,005 | 3/1993 | Doiron et al. . |
| 5,217,456 | 6/1993 | Narciso, Jr. . |
| 5,237,638 | 8/1993 | Narcisco, Jr. . |
| 5,237,985 | 8/1993 | Hodgson et al. . |
| 5,267,995 | 12/1993 | Doiron et al. . |
| 5,269,777 | 12/1993 | Doiron et al. . |
| 5,330,465 | 7/1994 | Doiron et al. . |
| 5,370,640 | 12/1994 | Kolff . |
| 5,441,497 | 8/1995 | Narciso, Jr. . |
| 5,454,794 | 10/1995 | Narciso et al. . |
| 5,588,952 | 12/1996 | Dandolu . |
| 5,624,432 | 4/1997 | Angelchik . |
| 5,698,866 | 12/1997 | Doiron et al. . |
| 5,722,426 | 3/1998 | Kolff . |
| 5,980,549 | 11/1999 | Chin ........................................ 606/190 |

FOREIGN PATENT DOCUMENTS

| | | |
|---|---|---|
| 0 311 295 A1 | 4/1989 | European Pat. Off. . |
| 0 617 912 A1 | 10/1994 | European Pat. Off. . |
| 0791332 A1 | 8/1997 | European Pat. Off. . |
| WO 97/32182 | 9/1997 | WIPO . |

OTHER PUBLICATIONS

Alper, "Transillumination: Looking right through you" *Science* (1993) 261:560.

Ambartsoumian, "Infrared transillumination gastroscopy" *Gastrointestinal Endoscopy* (1995) 41(3).

Angelini et al., "A fiber–optic retractor for harvesting the internal mammary artery" *Ann. Thorac. Surg.* (1990) 50(2):314–315.

Franzini et al., "Transillumination in minimally invasive surgery for carpal tunnel release" *J. Neurosurg.* (1996) 85:1184–1186.

Hung et al., "Clinical trail of a new lightwand device (Trachlight) to intubate the trachea" *Anesthesiology* (1995) 83(3):509–514.

Tevaearai et al., "Minimally invasive harvest of the saphenous vein for coronary artery bypass grafting" *Ann. Thorac. Surg.* (1997) 63:S119–S121.

*Primary Examiner*—Linda C. M. Dvorak
*Assistant Examiner*—Roy Gibson
*Attorney, Agent, or Firm*—Morrison & Foerster LLP

[57] ABSTRACT

A method of identifying vasculature including the steps of introducing an indicator in a peripheral vessel, and advancing a portion of the indicator into an internal vessel to identify said vessel. A catheter for identifying vasculature is also disclosed. The catheter is adapted to be introduced into a peripheral vessel and a portion thereof advanced into an internal vessel. The catheter includes a light delivery portion at a distal end thereof and an expandable member located proximal to the light delivery portion.

16 Claims, 12 Drawing Sheets

TRANSILLUMINATION CATHETER AND METHOD

FIELD OF THE INVENTION

The present invention relates generally to methods and devices for facilitating surgical procedures, and more particularly to methods and devices for transilluminating an internal blood vessel, artery or vein within a patient during a cardiac surgery procedure to facilitate locating and manipulating the vessel, artery or vein.

BACKGROUND OF THE INVENTION

Minimally invasive surgical techniques have revolutionized cardiac surgery. Minimally invasive cardiac surgery enjoys the advantages of reduced morbidity, quicker recovery times, and improved cosmesis over conventional open-chest cardiac surgery. Recent advances in endoscopic instruments and percutaneous access to a patient's thoracic cavity have made minimally invasive surgery possible. Reduction in morbidity, lower cost, and reduced trauma has made minimally invasive surgery desirable.

However, many problems and controversies still surround the viability of minimally invasive cardiac surgical procedures. One such problem is the difficulties of locating and manipulating small vessels, arteries, or veins in a closed-chest, blind environment during, for example, a minimally invasive coronary artery bypass graft (CABG) procedure. The coronary arteries typically have a diameter in the range of between about 1 to 5 mm, and the coronary bypass graft vessels have a diameter on the order of about 1 to 4 mm for an arterial graft such as a thoracic artery, or about 4 to 8 mm for a vein graft such as a saphenous vein. Locating and manipulating these tiny vessels is sufficiently difficult in conventional open-chest cardiac surgical procedures, and is made substantially more difficult in closed-chest, less invasive mini-thoracotomy procedures and in minimally invasive endoscopic procedures where the cardiac surgeon may not be able to view these vessels directly. Endoscopic instruments are currently used by the cardiac surgeon to view the internal thoracic cavity during a minimally invasive surgical procedure, but the use of these instruments alone has inherent drawbacks. For example, it is often difficult to differentiate the often tiny coronary arteries or coronary bypass graft vessels from other surrounding vessels and tissues with the use of endoscopic instruments alone during a minimally invasive surgical procedure.

An alternative technique for performing minimally invasive cardiac surgery procedures, therefore, is needed which facilitates locating and manipulating vessels by illumination from within the vessels. The technique should employ transillumination of a coronary vessel or coronary bypass graft vessel with light at predetermined wavelengths that are not substantially absorbed by the vessel itself, blood, other bodily fluids, or surrounding tissues and the like. The surgical technique can be applied for example, to the following areas, although it is to be understood that the present invention is by no means limited to these specific cardiac surgery procedures: (1) dissecting a left (or right) internal thoracic artery (LITA or RITA) from the chest wall in preparation for anastomosing the LITA to a native coronary vessel in a CABG procedure; (2) locating the LITA graft in a CABG repeat procedure; (3) locating the coronary artery to which a coronary bypass graft vessel is to be anastomosed; and (4) harvesting a free graft vessel, such as a saphenous vein, in preparation for anastomosing the free graft vessel to a native coronary artery in a CABG procedure. Each of these procedures will be explained in greater detail hereinafter.

Transillumination within the body of a patient has been recognized for at least a century. As long ago as the mid-1800's, British physicians began detecting scrotal cancer by holding a lamp behind the testes and noting the shadows the tumors cast. See "Transillumination: Looking Right Through You," Science, Vol. 261, Jul. 30, 1993 at page 560. Transillumination of the stomach was reported as early as 1911. Intraoperative transillumination of the small intestine and colon also is generally well known. See, e.g., Ambartsoumian, A., "Infrared Transillumination Gastroscopy," Gastrointestinal Endoscopy 1995:41(3) :270–71. Illuminators for transilluminating internal organs or vessels have been used in the fields of urology and gastroentology. An illuminator placed in the urethra or esophagus facilitates laproscopic and cystoscopic procedures by illuminating these organs thus avoiding unwanted damage to the organs. See, e.g., U.S. Pat. No. 5,624,432 to Angelchik (describing the preferred use of an illuminated bougie for illuminating the esophagus). Transillumination has also been used to facilitate the proper intracorporeal placement of catheters. See, e.g., U.S. Pat. No. 5,370,640 to Kolff, which discloses the use of a fiberoptic stylet device for facilitating the intracorpoeal placement of a retrograde coronary sinus catheter into the coronary sinus of a heart of a patient.

Although illuminators are generally well known by those skilled in the art, they typically have application for diagnostic or therapeutic purposes. Examples of such devices include the illuminators disclosed in U.S. Pat. No. 5,169,395 to Narciso, Jr., U.S. Pat. No. 5,196,005 to Doiron et al., U.S. Pat. No. 5,269,777 to Doiron et al., U.S. Pat. No. 5,330,465 to Doiron et al., U.S. Pat. No. 5,441,497 to Narciso Jr., and U.S. Pat. No. 5,454,794 to Narciso, Jr. et al. The devices described in those patents generally have the ability to deliver light to luminal surfaces such as blood vessels and are typically used for the diagnosis and treatment of a variety of medical conditions, with particular application to performing photodynamic therapy (PDT) in the treatment of diseased tissue such as tumors, inducing hyperthermia, or performing both percutaneous and intraoperative phototherapy of cardiovascular disease. However, despite the fact that transillumination has long been known, the present invention is believed to be the first use of transillumination to facilitate CABG surgery by any one of the methods described below.

SUMMARY OF THE INVENTION

The present invention discloses methods and devices for identifying vasculature. The identification methods and devices described herein can be used in conjunction with a combined technique involving laparoscopy and endoscopy to facilitate viewing and manipulating internal vessels during CABG and other cardiac surgery procedures. The techniques of the present invention can be used in open-chest coronary surgery where a partial or median sternotomy is used to gain access to the heart, in closed-chest less invasive coronary surgery procedures where a mini-thoracotomy is used to gain access to the heart, or in totally endoscopic procedures where a series of small holes, or ports, in the chest wall are used to gain access to the heart.

A method of the present invention is for identifying vasculature and generally comprises the steps of introducing an indicator in a peripheral vessel and advancing a portion of the indicator into an internal vessel to identify the vessel.

In another aspect of the invention, a catheter for identifying vasculature is adapted to be introduced into a peripheral vessel and a portion thereof advanced into an internal vessel. The catheter generally comprises a light delivery portion at a distal end thereof, and an expandable member located proximal to the light delivery portion.

In yet another aspect of the invention, a system for delivering energy to an internal vessel of a patient generally comprises a catheter and a catheter guide. The catheter comprises a flexible, elongated shaft having a proximal end, a distal end, and an energy transmitting diffuser located at the distal end of the shaft. The catheter guide has an opening which is sized and dimensioned to permit the catheter to be inserted longitudinally within the guide. The guide is configured for introduction into the peripheral vessel and advancement to the internal vessel to facilitate delivery of the catheter into the internal vessel.

Additional features and advantages of the invention will be set forth in or are apparent from the detailed descriptions of the preferred embodiments found herein below.

DESCRIPTION OF THE INVENTION

Figure 1:
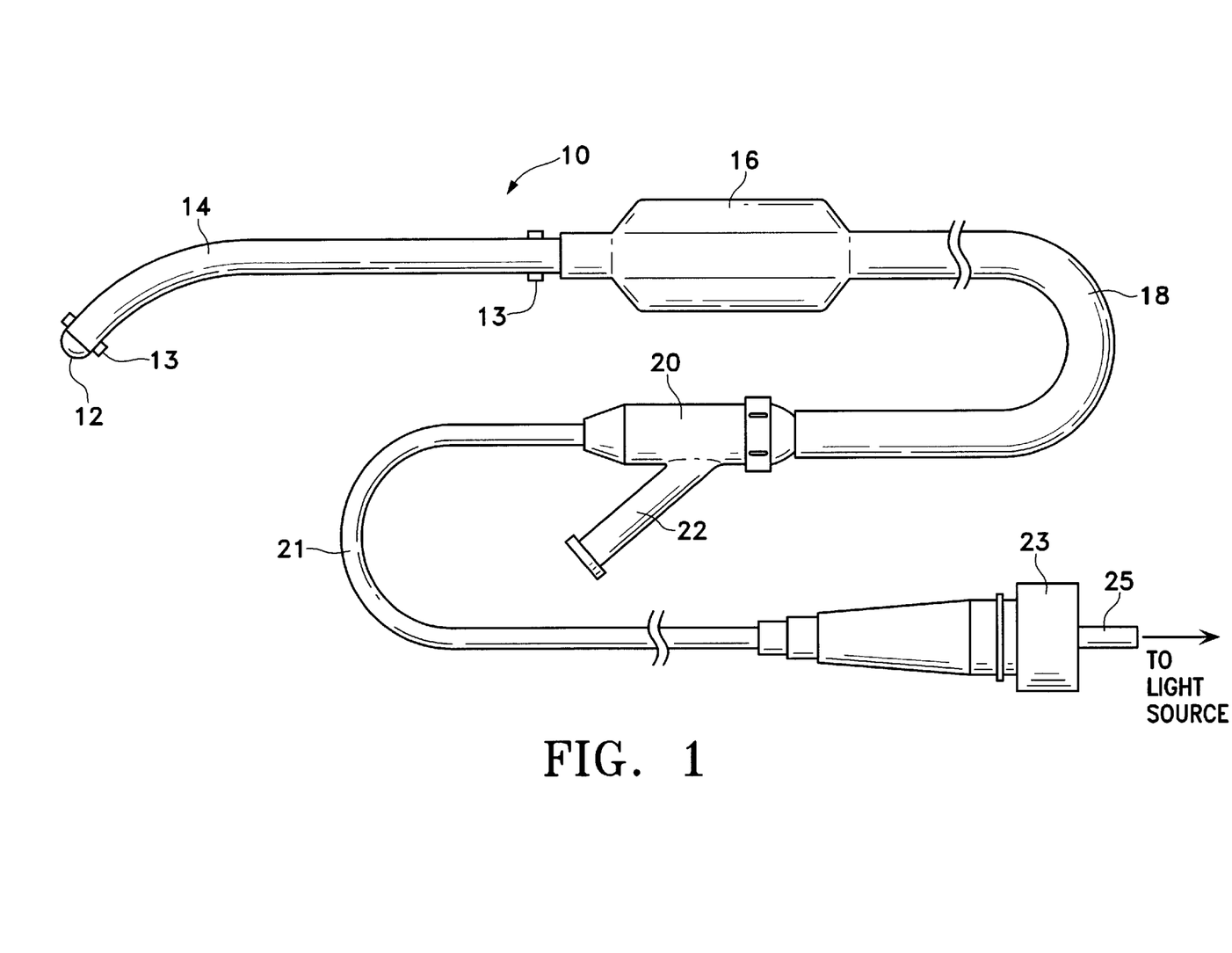
FIG. 1 is a schematic illustration of the transillumination catheter of the present invention.

Referring now to the drawings, and first to FIG. 1, an indicator for identifying vasculature is shown and is generally indicated by the reference numeral 10. The indicator 10 of the present invention is useful for delivering energy, such as visible, infrared, or ultraviolet light energy, to within a vessel, artery or vein during a coronary surgery procedure, such as a CABG procedure, to illuminate the vessel, artery or vein. Such transillumination of an internal vessel facilitates locating and manipulating the vessel during the surgical procedure. The indicator 10 can be used to facilitate open-chest coronary surgery procedures, closed-chest less invasive mini-thoracotomy surgery procedures, and totally endoscopic minimally invasive procedures.

The indicator 10 comprises a transillumination catheter having a light delivery portion for transmitting light to identify a vessel. The light is preferably diffused over a section of the distal end of the catheter 10 to sufficiently illuminate the vessel. The catheter 10 includes a fiber optic connector 23 at a proximal end of the catheter which is in optical communication with an energy source (not shown), such as a laser or a broad-band light source. In the latter case, a wavelength of between about 400 and 700 nm, and more preferably between about 600 and 700 nm, is preferred since this range of wavelengths will facilitate the emitted light energy to pass through bodily tissue. The fiber optic connector 23 can also be optically connected to an ultraviolet or infrared light energy source. Ultraviolet light typically has a wavelength of between about 100 and 400 nm, and infrared light typically has a wavelength of between about 700 and 15,000 nm. The light from the light source is delivered to a single optical fiber or bundle of optical fibers 25 enclosed within a first, inner catheter sheath 21. The optical fiber or bundle of optical fibers 25 is contained within and extends the length of the catheter 10 from the fiber optic connector 23 to the distal portion of the catheter 10 proximal to the light diffusing end member 14 of the catheter.

The catheter 10 includes a Y-shaped adapter 20 towards its mid-portion which is in fluid communication with an opaque, outer catheter sheath 18 which terminates at the proximal face of light diffusing end member 14. Inner catheter sheath 18 is sufficiently flexible to navigate tortuous vessels without great difficulty, and is preferably made from one or more biocompatible thermoplastic materials which have the optical and thermal properties required for this device to be operable such as Teflon®, polyurethane, polyethylene, polyethylene terephthalate, or other suitable biocompatible materials or combinations thereof.

The Y-shaped adapter 20 includes a balloon inflation/deflation port 22 through which a fluid may be administered and fluidly communicated through an inflation/deflation channel 30 (see FIG. 2) created between the external sheath 18 and inner sheath 21 to the balloon 16. The distal end of the transillumination catheter 10 includes a light diffusing end member 14 which is optically coupled to the distal face of optical fiber 25. The light diffusing end member 14 is marked by a pair of radiopaque markers 13 for visualization of the catheter 10 under x-ray fluoroscopy. Radiopaque markers 13 can be fabricated from gold, platinum, platinum-iridium, or any one of a number of other relatively dense materials. The distal portion of the catheter 10 is curved as shown to provide steering capabilities through a vessel which obviates the need for a distal guidewire or an internal steering wire or other steering mechanism. The shape of the distal portion of the catheter can be set thermally during processing or an additional coil (not shown) can be placed into the distal portion of catheter 10 as is well known by a person of ordinary skill in the art.

The transillumination catheter 10 is preferably dimensioned and configured for introduction into a peripheral vessel, such as a brachial artery 48 or radial artery 51 of a patient, and advanced to an internal thoracic artery of the heart (i.e., the LITA) through a subclavian artery (i.e., the left subclavian artery 90). This will generally require a catheter length of between about 20 to 60 cm. In addition, the catheter 10 may be configured to be inserted directly into a vein graft, such as a sapahenous vein, for illuminating the vein graft, in which case the catheter 10 will have a similar length of between about 20 to 60 cm. Alternatively, the catheter 10 may be adapted for introduction into a femoral artery 82 and advancement to a coronary or other vessel, such as an internal thoracic artery for example, wherein the catheter will need to be longer in length, for example about 90 to 120 cm. The catheter 10 may be adapted for introduction into several coronary arteries and other vessels, such as a right coronary artery 60, a left main coronary artery 58, a left anterior descending artery 64, a left circumflex 62, an aorta 56, and any branches of the left or right coronary artery (i.e., the posterior descending artery), from the same or other peripheral vessels such as a radial artery 51, left carotid artery 52, right carotid artery 54, brachial artery 48, left (or right) subclavian artery 90, or femoral artery 82, in which case its length will vary depending on the particular vessel and route of administration chosen. (See FIGS. 3–7).

Figure 2:
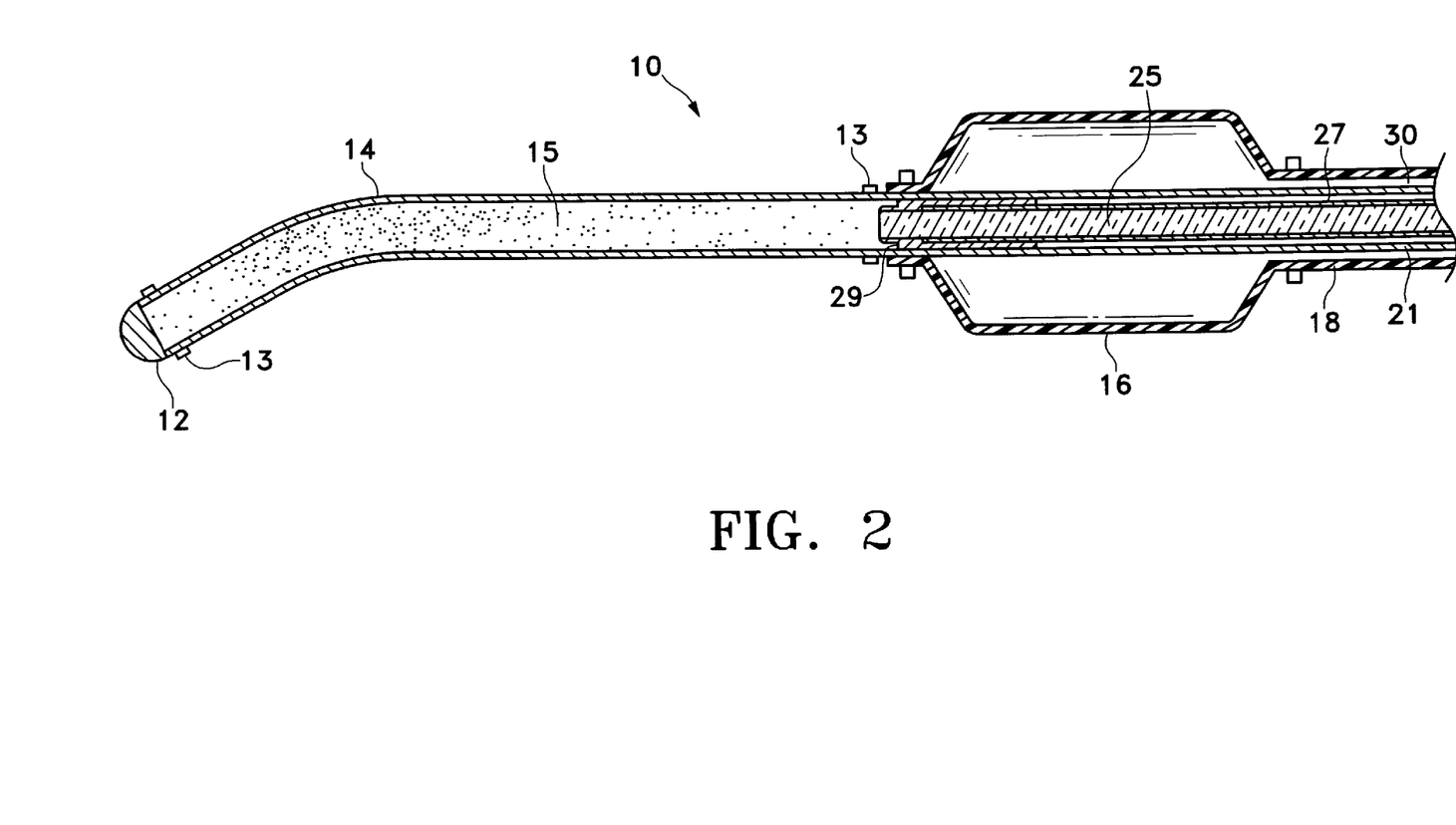
FIG. 2 is a longitudinal cross-sectional view of a distal end of the transillumination catheter of FIG. 1.

Referring now to FIG. 2, a longitudinal cross-sectional view of the distal end of the transillumination catheter 10 is shown. As seen in FIG. 2, optical fiber (or bundle of optical fibers) 25 is circumferentially surrounded by cladding 27 which promotes complete internal reflection of the light transmitted down the core of optical fiber 25. The distal portion of the cladding 27 is surrounded by an optical fiber centering sleeve 29. The light is transmitted from the distal face of optical fiber 25 to the light diffusing medium 15 encased within light diffusing end member 14. Light diffusing medium 15 is fabricated from an optically clear substrate such as silicone with optical scattering centers distributed within the substrate. The optical scattering centers can be fabricated from alumina, silica, titanium oxide, calcium carbonate, or other suitable materials. By varying the concentration of scattering centers in the light diffusing medium 15 from lowest at the optical fiber 25 to greatest at the rounded cap 12, as shown, either discretely or continuously, the light output distribution from the light diffusing end member 14 can be made both radially and axially uniform. Alternatively, the optical scattering centers can be uniformly distributed throughout light diffusing medium 15.

Figure 4:
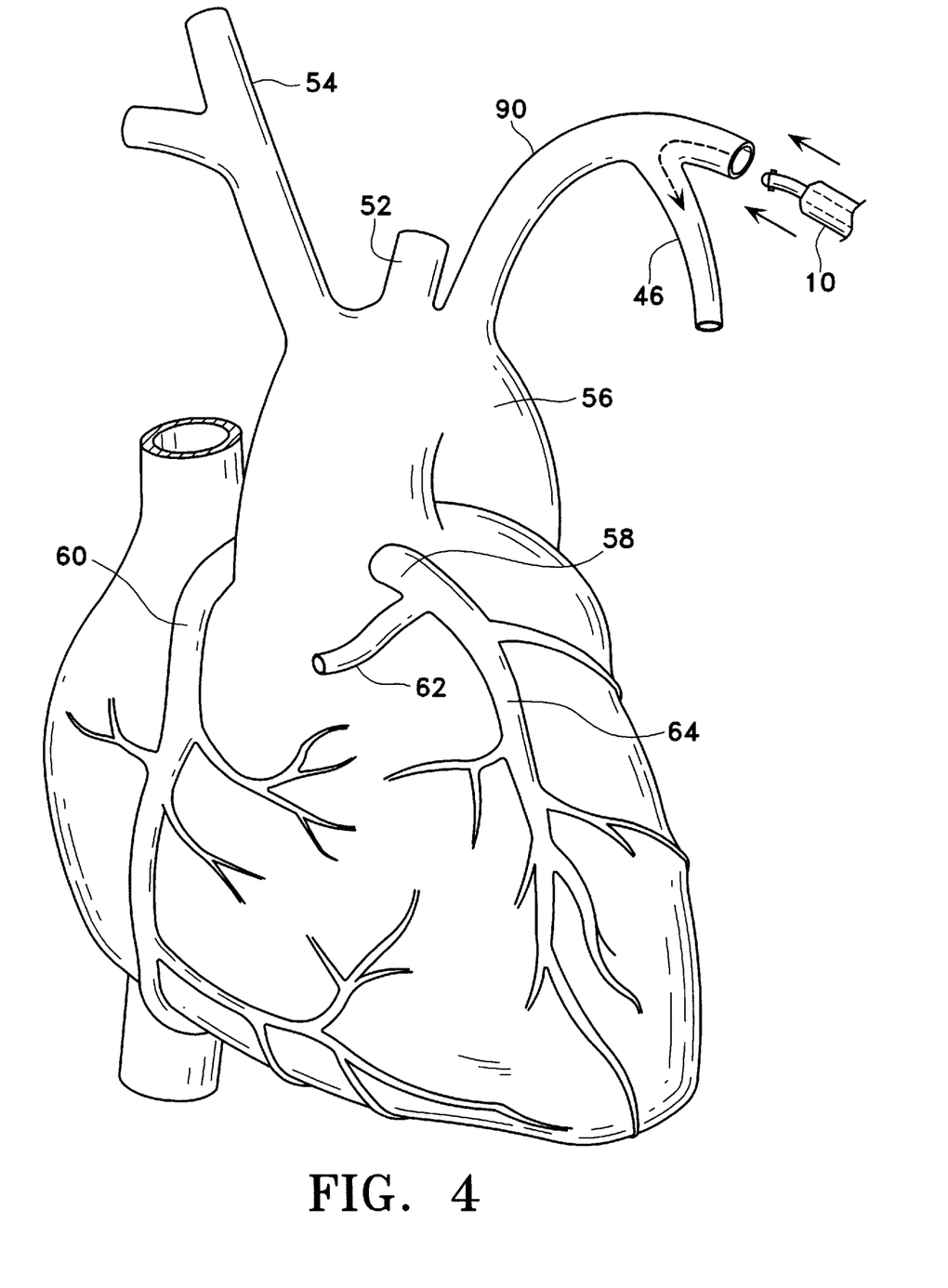
FIG. 4 is an enlarged view of a patient's heart schematically showing the transillumination catheter disposed within a subclavian artery and being advanced towards the left internal thoracic artery.

The transillumination catheter 10 shown in FIGS. 1–2 can be used in any one of several novel ways to facilitate locating and manipulating vessels, arteries or veins in coronary surgery procedures. FIG. 4 shows one such novel use of transillumination catheter 10 for locating and illuminating a LITA graft vessel 46 prior to dissecting the LITA graft from the chest wall in preparation for a CABG procedure. The LITA transillumination technique can be used in open-chest coronary surgery where a partial or median sternotomy is used to gain access to the heart or in closed-chest less invasive coronary surgery procedures where a mini-thoracotomy is used to gain access to the heart The harvest of the LITA 46 (or RITA 45) for coronary bypass grafting can also be performed thoracoscopically through three small skin incisions as fully described in Duhaylongsod, F. G. M.D., Mayfield, W. R. M.D., Wolf, R. K. M.D., "Thoracoscopic Harvest of the Internal Thoracic Artery for Coronary Bypass Grafting: A Multi center Experience in 219 Cases," presented at the "Facts & Myths of Minimally Invasive Cardiac Surgery: Current Trends in Thoracic Surgery IV" symposium before the 34$^{th}$ Annual Meeting of the Society of Thoracic Surgeons, New Orleans, La., Jan. 24, 1998, the entire contents of which are incorporated by reference herein. The following is an exemplary usage of the LITA transillumination technique in a standard mini-thoracotomy procedure.

Figure 3:
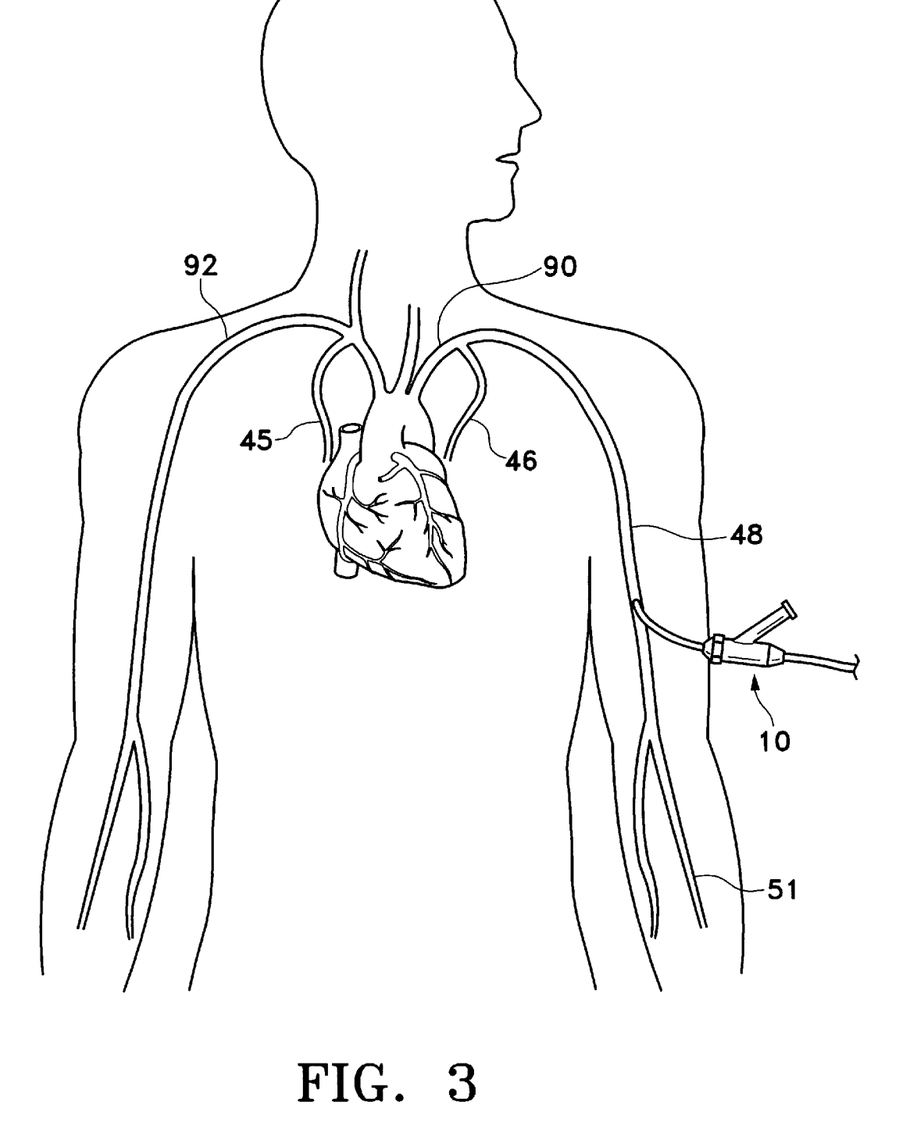
FIG. 3 schematically illustrates insertion of the transillumination catheter into a brachial artery of a patient for advancement to a left internal thoracic artery via a left subclavian artery.

A transillumination catheter, such as catheter 10 in FIGS. 1–2, is first percutaneously inserted into a peripheral vessel, such as a brachial artery 48, by conventional means and advanced with the aid of x-ray fluoroscopy into the LITA 46 via a subclavian artery to provide illumination of the LITA, as schematically illustrated in FIGS. 3–4. As noted above, the catheter 10 can also be percutaneously inserted into other peripheral vessels as well, such as a radial artery 51 or a femoral artery 82, by a suitable technique, such as the Seldinger technique, and advanced through a subclavian artery into the LITA (or other coronary vessel). Applicants have demonstrated that the use of a transillumination catheter placed within the LITA helps to facilitate the procedure of locating, manipulating and dissecting the LITA from the chest wall without damage or unnecessary morbidity to the surrounding tissues and body structures.

After establishment of general anesthesia with a double-lumen endobronchial tube, for example, allowing complete collapse of the left or right lung, the left lung is deflated to allow access to the heart and LITA. A 6 to 8 cm left anterior thoracotomy incision is then made in the patient's chest in the fourth intercostal space. Other sites may be suitable depending on the patient's anatomy, such as the fifth or sixth intercostal space. A retractor is used to spread apart the ribs to provide access to the heart and the LITA. The LITA is then dissected under direct vision with suitable instruments introduced through the thoractomy incision, such as scissors, pliers and the like. The balloon 16 of catheter 10 is used to internally seal the LITA graft vessel prior to transecting the distal end of the LITA graft in preparation for the coronary anastomosis procedure. This obviates the need for using external clamps to provide hemostasis within the graft vessel prior to transection. Following dissection of the LITA, the resulting LITA pedicle is transected with a suitable instrument such as scissors through the thoracotomy. Papaverine is then injected directly through the LITA, which is prepared for coronary anastomosis to a stenotic coronary artery 64. The anastomosis of the LITA to the coronary artery is then performed directly through the thoracotomy incision by using conventional suturing means, or by using a novel distal anastomosis device and procedure such as described below in connection with FIGS. 8–13 and in co-pending patent application for Anastomosis Device and Method, filed on Mar. 9, 1998, and invented by Hugh Narciso, Jr.

If required, cardiac stabilization such as described in co-pending provisional patent application Ser. No. 60/055, 127, for Compositions, Apparatus and Methods for Facilitating Surgical Procedures, filed Aug. 8, 1997, and invented by Francis G. Duhaylongsod, M.D., may be used during the procedure. Other pharmacological or mechanical methods may also be used.

Figure 5:
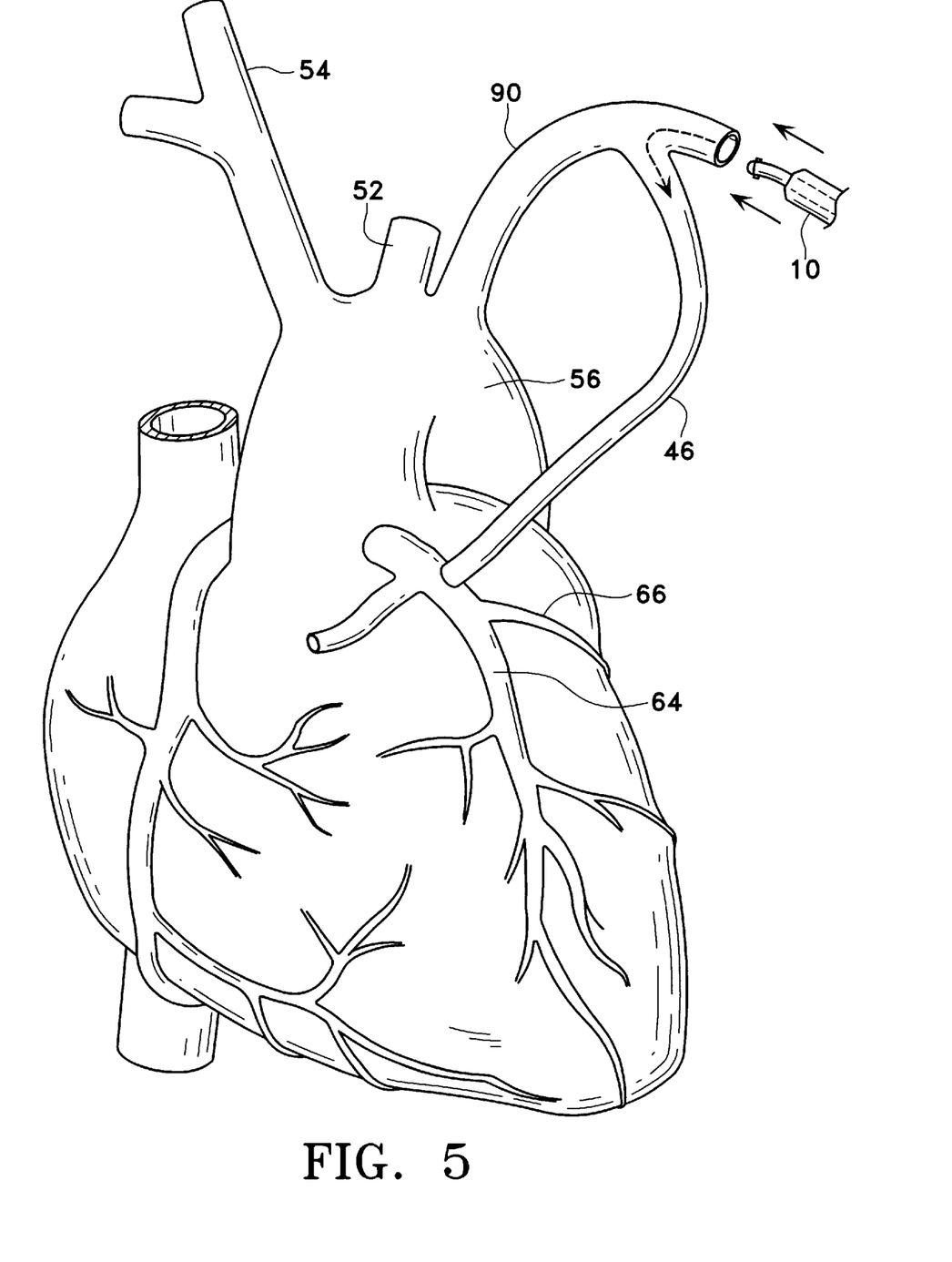
FIG. 5 is an enlarged view of a patient's heart schematically showing the transillumination catheter disposed within a subclavian artery and being advanced towards the left internal thoracic artery in a repeat CABG procedure.

A second preferred intended novel use of the present invention is for locating the LITA, for example, in a repeat coronary surgical procedure, such as in a redo CABG procedure, to prevent injury while attempting to correct an imperfect anastomosis graft between the LITA and a stenotic native coronary artery, such as the LAD. As noted above, locating the LITA during repeat CABG surgery, for example, is critical to the safety of the patient because the graft LITA represents one of the major supplies of blood to the heart. When the LITA is anastomosed to the LAD, for example, it typically is placed across the anterior surface of the heart, directly under the sternum, as shown in FIG. 5. If a second, or redo, CABG procedure needs to be performed, the cardiac surgeon typically needs to bisect the sternum to gain access to the heart. Often in doing so, the surgeon inadvertently compromises the LITA graft 46 and the patient has limited alternatives if the LITA graft cannot be repaired.

To alleviate this concern, as described above, a transillumination catheter, such as catheter 10 in FIGS. 1–2, is percutaneously inserted into a peripheral vessel, such as a brachial artery 48 or radial artery 51, and advanced into the LITA 46 via a subclavian artery 90 to provide illumination of the LITA, as schematically illustrated in FIG. 5. We have demonstrated that light diffusing from a transillumination catheter at a specific wavelength or wavelengths (for example, at a wavelength of between about 400 and 700 nm, and more preferably between about 600 and 700 nm) which is placed within the lumen of the LITA graft vessel is completely visible through the chest wall of the patient. With a transilluminator catheter in place and the LITA graft 46 illuminated, using current techniques, a surgeon can accurately perform a partial or median sternotomy to gain access into the patient's thoracic cavity while avoiding the illuminated LITA graft vessel, thus obviating difficulties associated with a compromised LITA graft 46. A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart to correct the imperfect anastomosis or diseased graft vessel.

Figure 6:
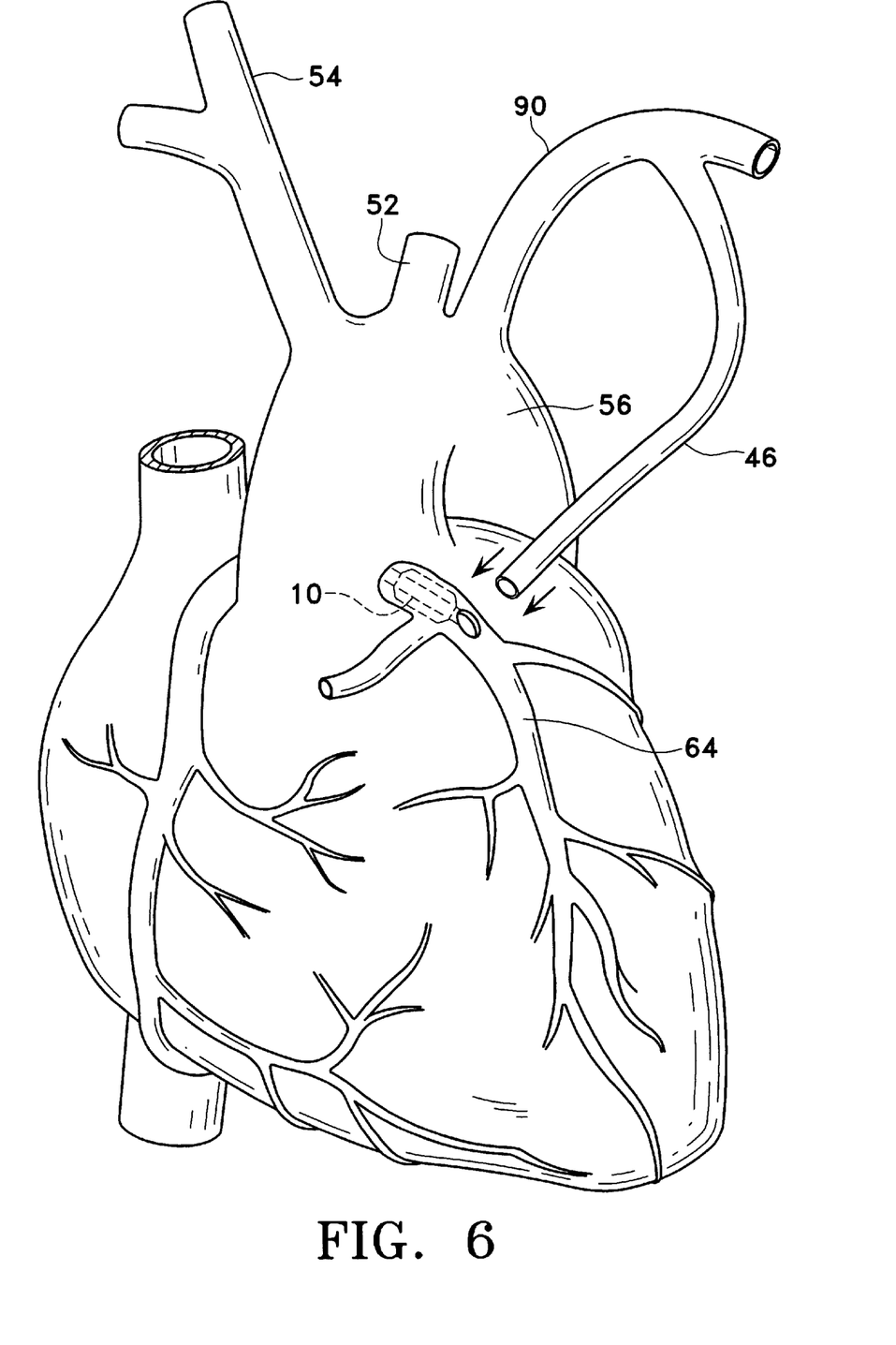
FIG. 6 is an enlarged view of a patient's heart schematically showing the transillumination catheter disposed within a stenotic coronary artery.

Another preferred intended novel use for the present invention is for locating and manipulating stenotic coronary vessels to which a graft vessel is being anastomosed in a CABG procedure. When performing CABG surgery, the stenotic native coronary artery to which a graft vessel is being anastomosed is obscured by surrounding fat or cardiac tissues. The cardiac surgeon must cut through tissues to access the coronary artery for purposes of creating a clear field of view to perform the anastomosis procedure. In some instances, it is possible for the cardiac surgeon to compromise the stenotic coronary artery while attempting to cut through the fat and cardiac tissues. However, with a transilluminator catheter in place within the coronary artery, the cardiac surgeon will be able to dissect the surrounding tissues from the coronary artery thus exposing the artery for the anastomosis procedure. In this preferred use of catheter 10, the catheter 10 is percutaneosuly inserted into a peripheral vessel, such as a brachial artery 48 or radial artery 51, as schematically illustrated in FIG. 6. Illumination of the transillumination catheter 10 will help the surgeon to visualize the stenotic coronary artery such as a stenotic left anterior descending artery 64 while the graft vessel, such as the LITA pedicle 46 shown in FIG. 6, is being anastomosed to it.

Figure 7:
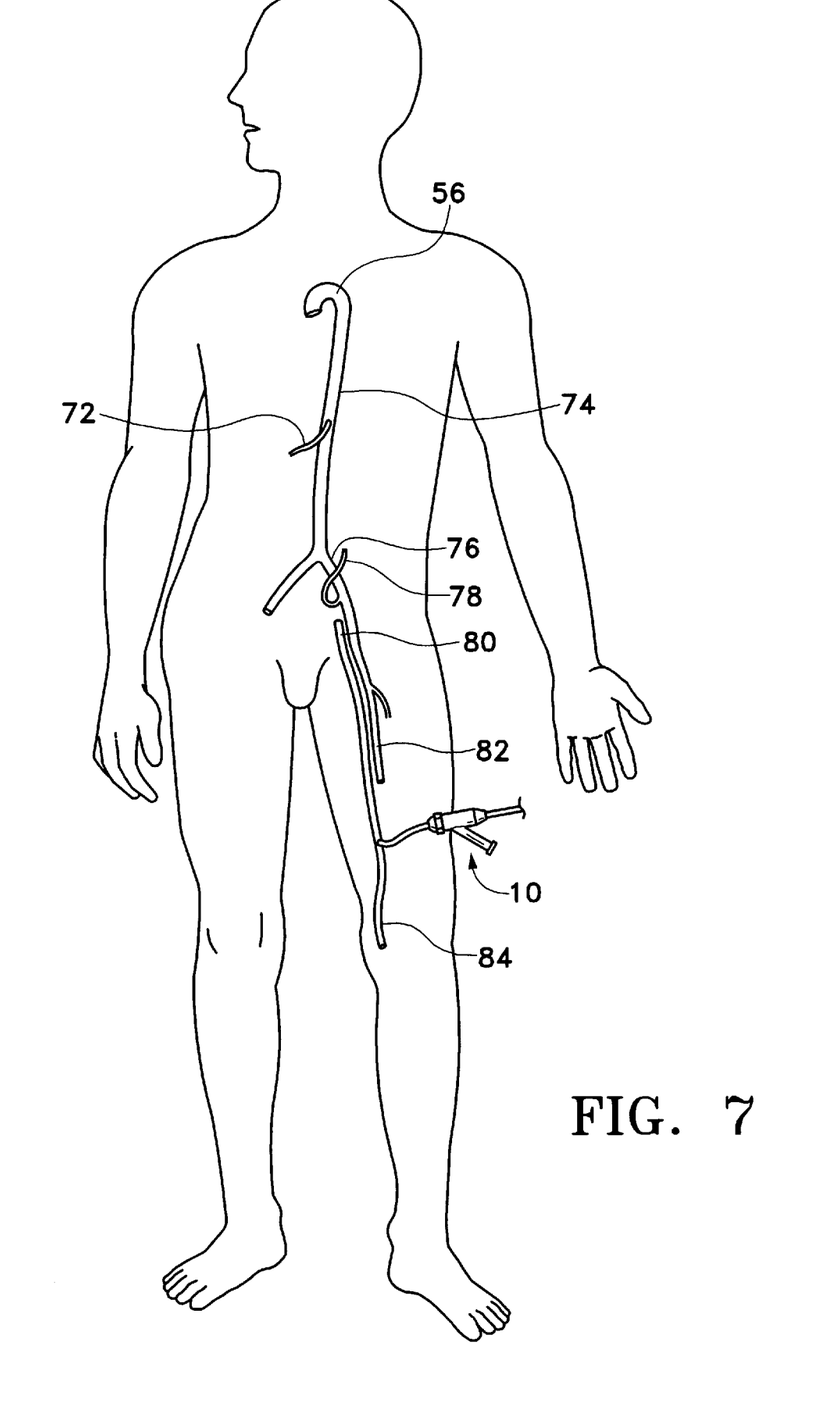
FIG. 7 schematically illustrates insertion of the transillumination catheter of FIG. 1 into a saphenous vein of a patient for illumination of the vein prior to harvesting it for a coronary anastomosis procedure, along with showing other vessels which can be illuminated.

FIG. 7 schematically illustrates another preferred novel use of the transillumination catheter 10 of the present invention for harvesting a free vessel graft, typically a saphenous vein 84, from a patient undergoing a CABG procedure. FIG. 7 illustrates the location of various vessels, including the abdominal aorta 74, the common iliac artery 76 and the femoral vein 80. A transilluminator catheter 10 is percutaneously inserted under the skin and inserted into a saphenous vein 84. With the transilluminator in place and the saphenous vein 84 illuminated, a surgeon gently dissects the saphenous vein 84 with suitable surgical instruments, such as scissors and the like. The device may be used to transilluminate other bypass graft vessels such as a gastroepiploic artery 72 or an inferior epigastric artery 78. The use of a transillumination device placed within the vein to be harvested makes the harvesting procedure simpler and facilitates location and extraction of the graft vessel. The transillumination catheter can be used in combination with conventional endoscopic techniques to simplify the process of harvesting the vein graft in an endoscopic procedure.

Figure 8:
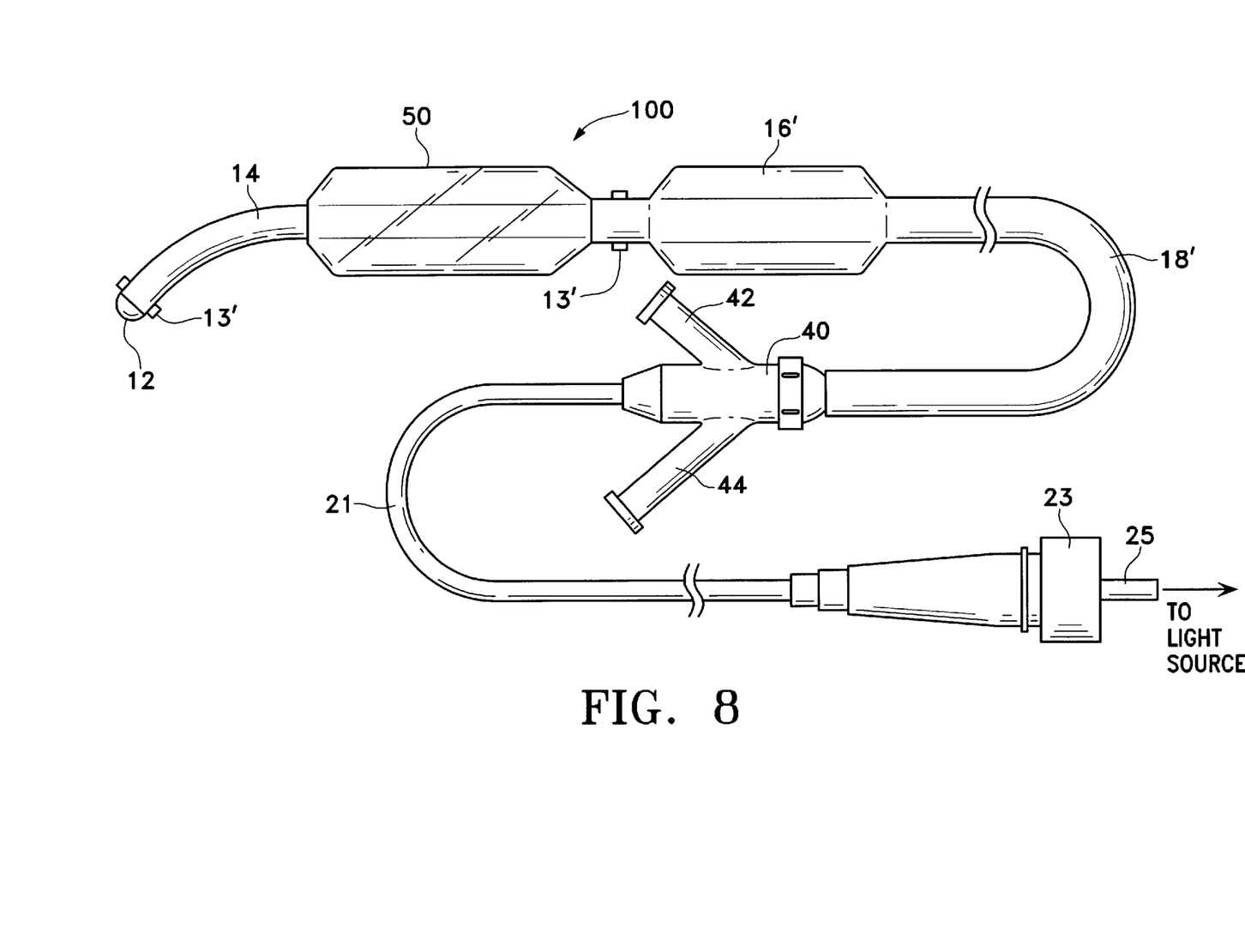
FIG. 8 is a schematic diagram of an alternative embodiment of the transillumination catheter of FIG. 1.

FIG. 8 illustrates an alternative embodiment of the transillumination catheter 10 of FIGS. 1–2 generally indicated by reference numeral 100, wherein like numerals represent like parts. For example, the optical fiber 25, fiber optic connector 23, catheter sheath 21, and light diffusing end member 14 have the same general function and arrangement as described in FIGS. 1–2. Transillumination catheter 100 can be used to facilitate the coronary surgical procedures described above akin to catheter 10, and can also be used to facilitate joining a transected graft vessel to a stenotic target vessel in a coronary anastomosis, as will be described in greater detail below.

As shown in FIG. 8, the Y-adapter 20 of catheter 10 is replaced with a three arm adapter 40 which incorporates two separate and independent balloon inflation/deflation ports 42, 44 which allow the addition of fluid, such as saline, through an inflation/deflation channel (not shown) defined by outer sheath 18' to the distal balloons 16' and 50, respectively. Balloon 50 is affixed to the outer sheath 18' so that the balloon 50 overlies a substantial portion of the light diffusing end member 14 of catheter 100. The wall of the balloon 50 is transparent at the wavelength of light being delivered to (or received from) the surrounding tissue from light diffusing end member 14. Distal and proximal to balloon 50 are radiopaque marker bands 13' for visualization under x-ray fluoroscopy. The provision of a second balloon 50 is advantageous where the transillumination catheter 100 of the present invention is used in connection with a novel distal anastomosis device disclosed in co-pending patent application for "Anastomosis Device and Method," filed on Mar. 9, 1998, and sharing a common inventor (Hugh L. Narciso, Jr.), the entire contents of which are fully incorporated by reference herein.

As described therein, an anastomotic fastener is disclosed which in one embodiment comprises a tubular sleeve formed of a deformable material, such as a light-activated polymeric material (i.e., a polycaprolactone material) which becomes formable (i.e., fluent) upon the application of light energy to the material at a specific frequency, wavelength or wavelengths. The anastomotic fastener is configured to be positioned radially adjacent a free end portion of a graft vessel, such as a LITA graft, which is then preferably everted over a portion of the tubular sleeve. The deformable material may be selectively irradiated and molded in vivo by providing an energy source that produces radiation at a frequency, wavelength, or wavelengths that are readily absorbed by the material. Radial expansion of the graft vessel will permit the deformable material in its moldable state to be shaped such that the free end portion of the graft vessel in its everted configuration is in secure conforming engagement with an inner wall of the target vessel, resulting in an intima-to-intima anastomosis. Transillumination catheter 100 can be used in lieu of the light-diffusing catheter described in the subject co-pending patent application to irradiate and radially expand the anastomotic fastener device.

Figure 9:
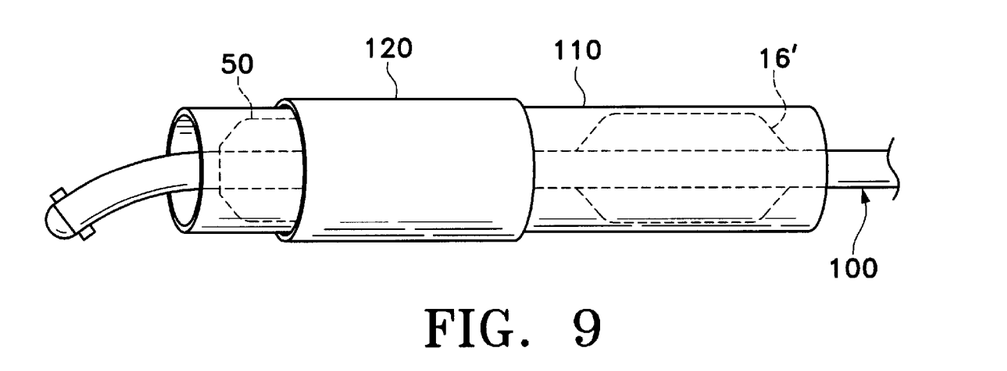
FIG. 9 shows the transilluminator catheter device of FIG. 8 positioned within a LITA graft vessel which has an anastomotic fastener positioned about an external surface of a free end portion of the graft vessel.
Figure 10:
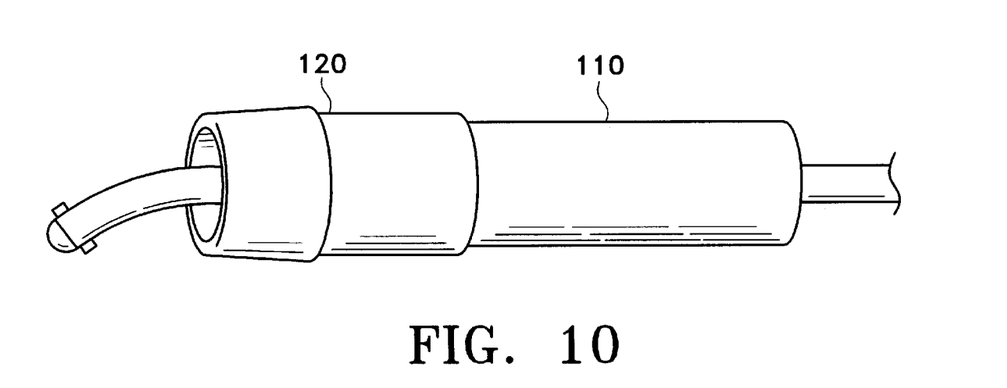
FIG. 10 shows the free end portion of the graft vessel everted over a portion of the anastomotic fastener.
Figure 11:
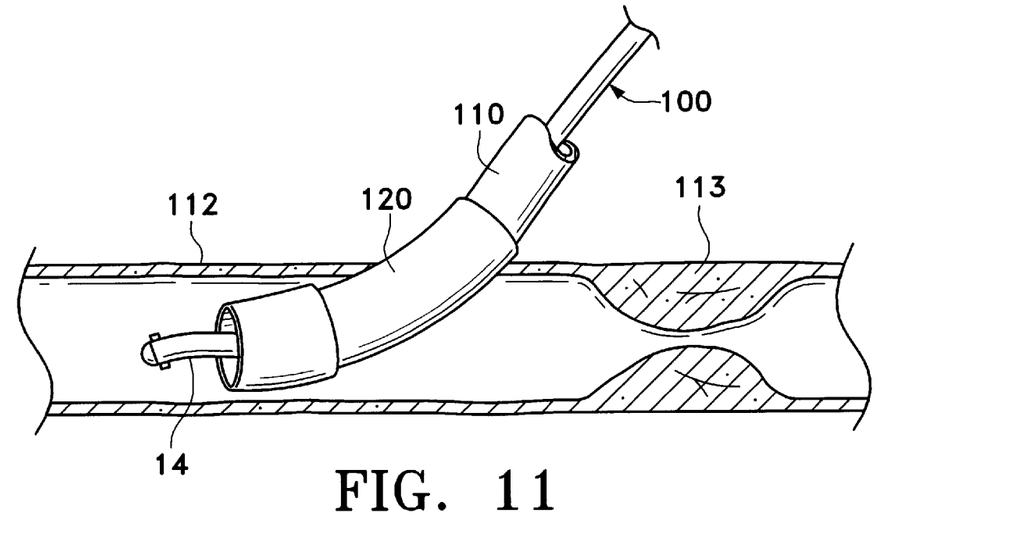
FIG. 11 shows the graft vessel with the transillumination catheter of FIG. 8 positioned therein being inserted into the target vessel through an incision in the target vessel.
Figure 12:
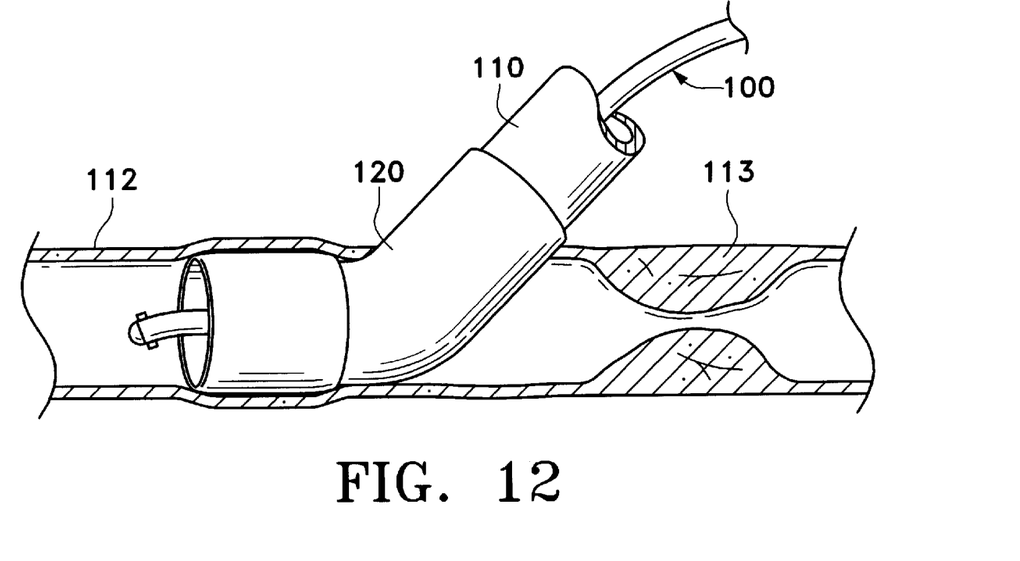
FIG. 12 is an elevated view of the anastomotic fastener following light irradiation and radial expansion of a balloon of the transillumination catheter.
Figure 13:
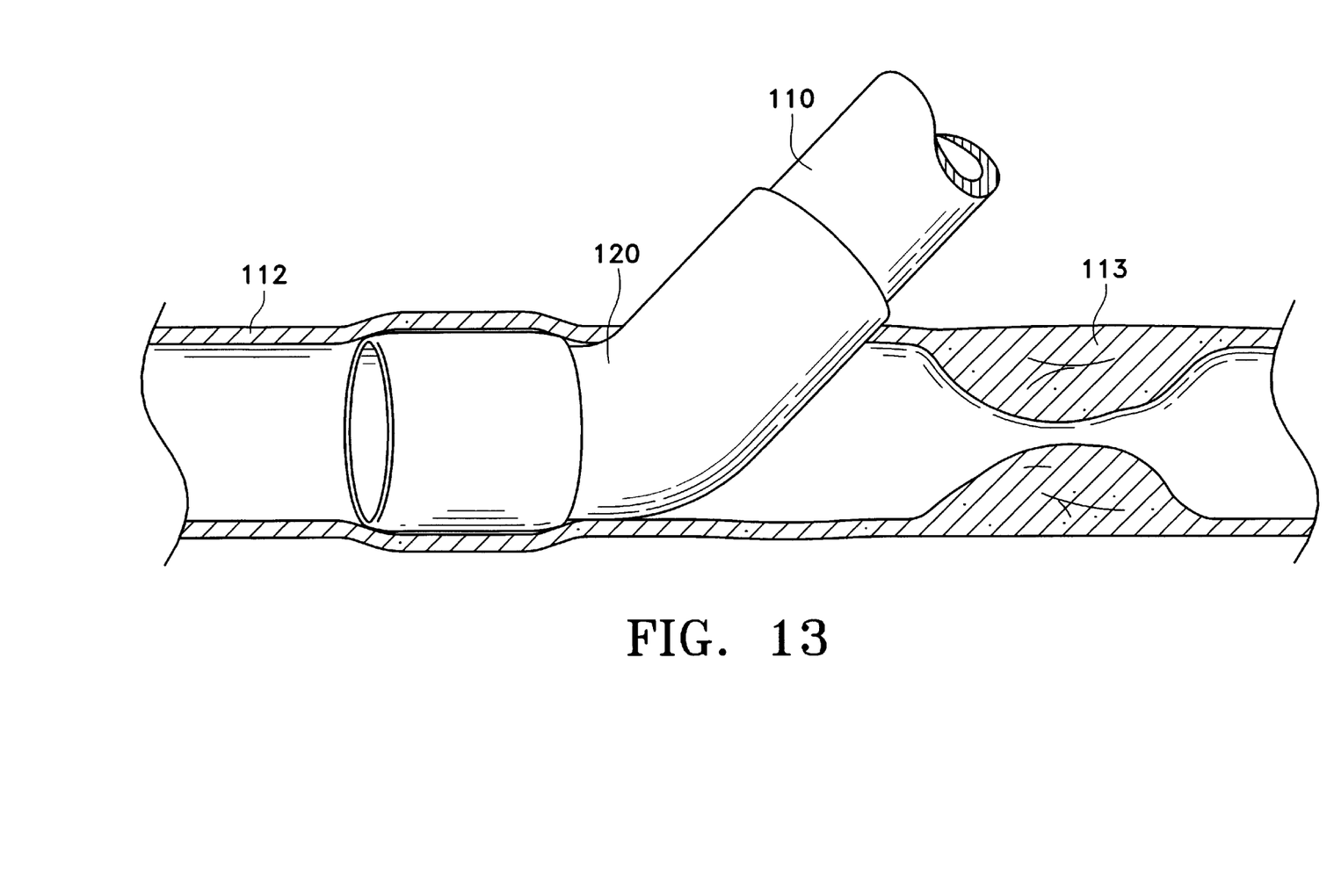
FIG. 13 is an elevated view of the anastomotic fastener after the transillumination catheter has been removed from the graft vessel showing the completed anastomosis.

For example, with reference to FIGS. 9–13, transillumination catheter 100 is first inserted into a LITA graft vessel 110 in a similar fashion as described above in connection with FIGS. 3–4, and the LITA graft vessel 110 can be illuminated and then dissected and transected using balloon 16' to seal the LITA prior to transecting it. With a free end portion of the LITA graft vessel 110 exposed as shown in FIG. 9 and balloon 16 expanded to occlude the vessel, a deformable anastomosis fastener device 120 can be positioned about an external surface of (or inserted into) a free end portion of the LITA graft 110, which preferably is then everted over a portion of the tubular sleeve 120 (see FIGS. 9–10). The LITA graft vessel 110 is then inserted into a target vessel 112, such as an LAD having a stenotic region 113, through an incision in a wall of the target vessel 112.

With the anastomotic fastener 120 securely positioned in the target vessel 112, light energy at a given wavelength or wavelengths is supplied to the light diffusing end member 14 of catheter 100 from the energy source (not shown) via optical fiber 25 to irradiate, or illuminate, the tubular member 120 with light at a wavelength or wavelengths at which the deformable material readily absorbs. Upon absorption of the light energy, the deformable material forming tubular member 120 is transformed into its moldable, fluent state. Inflation of the balloon 50 causes the tubular member 120 to radially expand outwardly, thereby pressing the LITA graft vessel 110 into conforming engagement with an inner wall of target vessel 112 (see FIG. 12). If it is necessary to move catheter 100 longitudinally within the graft vessel 110 to, for example, precisely position balloon 50 radially adjacent tubular member 120, balloon 16' can be deflated slightly. This will permit longitudinal movement of the catheter 100 within the graft vessel 110, at which point balloon 16' can then be re-inflated fully to firmly seal the graft vessel 110 and prevent blood flow into the anastomosis site. By discontinuing the supply of light energy from the energy source, the deformable material will become non-fluent and remain in its molded configuration. Both balloons 16', 50 are then deflated and the catheter device 100 is withdrawn from the LITA graft vessel 110 to complete the anastomosis (see FIG. 13).

Figure 14:
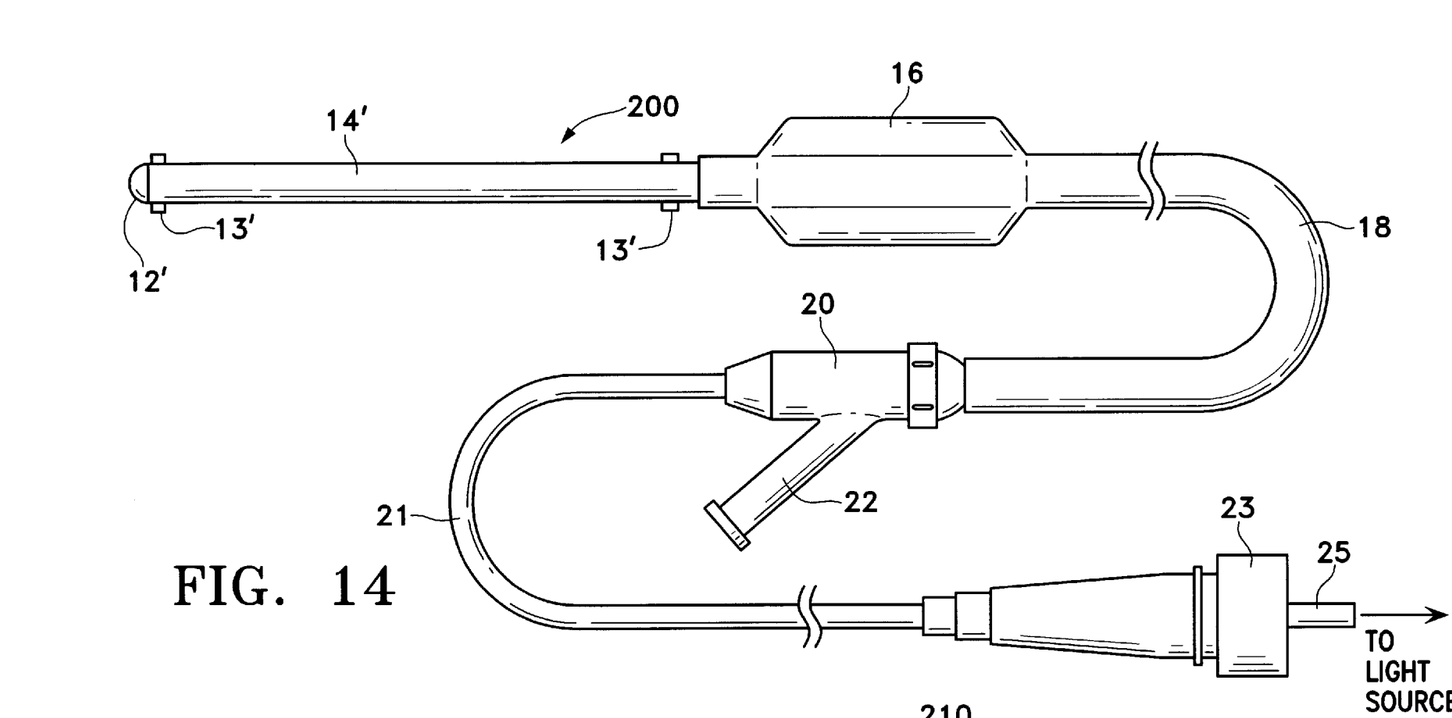
FIG. 14 is a schematic diagram of an alternative embodiment of the transillumination catheter of FIG. 1.

FIG. 14 is a third alternative embodiment of a transillumination catheter generally indicated by reference numeral 200. The transillumination catheter 200 is similar in most respects to the transillumination catheter 10 of FIGS. 1–2, except that the distal end of the catheter 200 is substantially straight, and does not have a curved configuration as does the distal end of catheter 10. A catheter guide 205 is shown in schematic form in FIG. 15. The guide 205 comprises a flexible, elongate tubular body 210 which is sized and dimensioned to permit catheter 200 to be longitudinally inserted within the tubular body 210. Tubular body 210 may be manufactured from any suitable, relatively flexible biocompatible plastic such as polyethylene, polyurethane, silicone, and the like. The guide 205 facilitates placement of transillumination catheter 200 within an internal vessel, such as a LITA graft vessel. The catheter 200 may be formed with a guide wire lumen (not shown) as described in U.S. Pat. No. 5,169,395, which is incorporated herein by reference. The lumen may be used for insertion of a guidewire or insertion of a fluoroscopic dye to assist in guiding the catheter.

Figure 15:
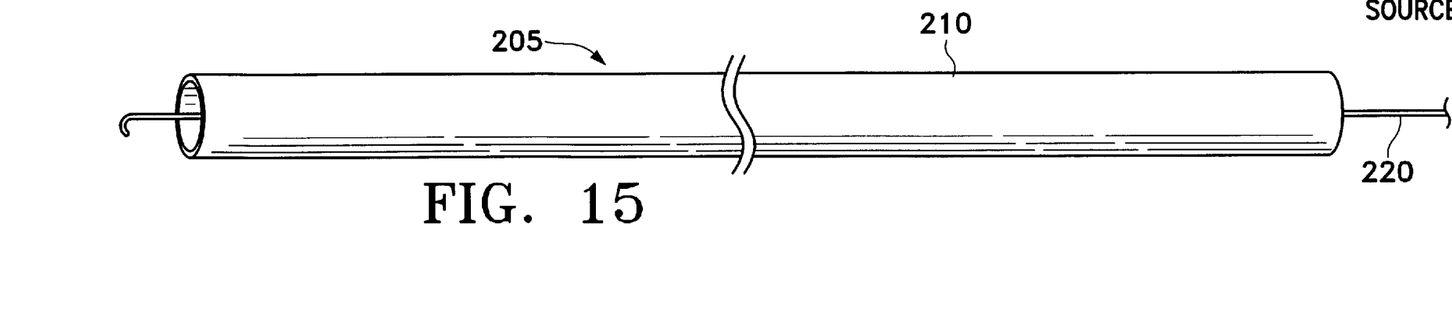
FIG. 15 is a schematic illustration of a catheter guide and guide wire for facilitating placement of the transillumination catheter into an internal vessel.

In use of the above system, the guide 205 is first percutaneously inserted into a peripheral vessel, such as a brachial artery 48, radial artery 51 or femoral artery 82, and advanced over a guidewire 220 by conventional means to an internal vessel, such as LITA graft vessel. With the distal end of tubular body 210 positioned a short distance within the internal vessel, the guidewire 220 is pulled back and removed from tubular body 210. Subsequently, transillumination catheter 200 can be longitudinally inserted into tubular body 210 and advanced transluminally through it such that the light transmitting diffusing end member 14' is placed within the internal vessel and extends beyond the distal end of the tubular body 210. Alternatively, tubular body 210 may be advanced into the internal vessel to a position at which transillumination of the vessel is required. Subsequently, the distal end of transillumination catheter 200 is advanced up to the distal end of tubular body 210, and the tubular body 210 is then pulled back a short distance over the transillumination catheter 200 to expose the light transmitting distal end member 14' of the catheter 200. The transillumination catheter 200 is then used to illuminate the internal vessel as described above. The guide 205 is advantageous in that it can be used to effectively guide catheter 200 into an internal vessel, obviating the need to shape the distal end of catheter 200 or to provide a guidewire or other steering mechanism within catheter 200.

It should be understood that while the above is a complete description of the preferred embodiments of the invention, various alternatives, modifications and equivalents may be used. Therefore, the above description should not be taken as limiting the scope of the invention which is defined by the following claims.

What is claimed is:

1. A method of identifying viable vasculature for dissection comprising introducing a catheter having a light delivery portion in a peripheral vessel which is not a coronary vessel, advancing a portion of the catheter into an internal vessel to identify said vessel, and dissecting at least a portion of the vessel after advancing the catheter.

2. The method of claim 1 further comprising the step of activating the light delivery portion to transmit light and identify the vessel.

3. The method of claim 2 further including the step of diffusing the transmitted light.

4. The method of claim 3 wherein the light has a wavelength in the range of 100 to 1100 nm.

5. The method of claim 3 wherein the light has a wavelength in the range of 400 to 700 nm.

6. The method of claim 3 wherein the light has a wavelength in the range of 600 to 700 nm.

7. The method of claim 2 further comprising the step of occluding blood flow through the internal vessel.

8. The method of claim 7 wherein said catheter comprises a balloon and said step of occluding comprises expanding the balloon.

9. The method of claim 1 wherein the peripheral vessel is a brachial artery, a radial artery, a femoral artery, or a carotid artery.

10. A method of identifying vasculature comprising:
   introducing a catheter having a light delivery portion and a balloon in a peripheral vessel;
   advancing the light delivery portion of the catheter into an internal vessel;
   activating the light delivery portion to transmit light to identify said vessel;
   occluding blood flow through the internal vessel by expanding said balloon; and
   transecting a distal end of said internal vessel in preparation for a coronary anastomosis after expanding the balloon.

11. The method of claim 10 wherein said internal vessel is an internal thoracic artery and further comprising the step of sealingly joining a free end of said internal thoracic artery to a stenotic coronary artery after transecting the distal end of said internal thoracic artery.

12. The method of claim 10 wherein the peripheral vessel is a brachial artery, a radial artery, a femoral artery, or a carotid artery.

13. The method of claim 11 wherein the peripheral vessel is a brachial artery, a radial artery, a femoral artery, or a carotid artery.

14. The method of claim 10 wherein the internal vessel comprises a bypass graft vessel.

15. The method of claim 14 wherein the bypass graft vessel is a gastroepiploic artery or an inferior epigastric artery.

16. A method of identifying vasculature comprising introducing an indicator in a peripheral vessel, advancing a portion of the indicator into an internal thoracic artery to identify said internal thoracic artery, and separating a sternum after advancing the indicator.

* * * * *